United States Patent [19] [11] 4,237,066
Barton [45] Dec. 2, 1980

[54] PREPARATION OF LOWER ALKYL THIOSEMICARBAZIDES

[75] Inventor: Danny B. Barton, Kansas City, Mo.

[73] Assignee: Mobay Chemical Corporation, Pittsburgh, Pa.

[21] Appl. No.: 955,283

[22] Filed: Oct. 26, 1978

[51] Int. Cl.³ .......................................... C07C 159/00
[52] U.S. Cl. ..................................................... 564/18
[58] Field of Search ................................ 260/552.5 C

[56] References Cited

U.S. PATENT DOCUMENTS 3,929,877  12/1975  Toth et al. ..................... 260/552 SC
4,132,736  1/1979   Cremm et al. ................. 260/552 SC

FOREIGN PATENT DOCUMENTS 138018  8/1970  Czechoslovakia.
832891  8/1956  Fed. Rep. of Germany.

OTHER PUBLICATIONS

Jesen et al., Acta Chem. Scano. 22, 15 (1968).

Primary Examiner—Thomas A. Waltz
Attorney, Agent, or Firm—Sprung, Felfe, Horn, Lynch & Kramer

[57] ABSTRACT

A process for the production of a lower alkyl-thiosemicarbazide comprising steam distilling an aqueous solution containing hydrazine and an N-lower alkyl-dithiocarbamic acid quaternary ammonium salt thereby to effect pyrolysis while distilling off water, lower alkyl amine and hydrogen sulfide, and cooling the distilland to form crystals of the lower alkylthiosemicarbazide. Advantageously the solution is obtained by reacting carbon disulfide and methylamine in water, followed by addition of hydrazine.

6 Claims, No Drawings

PREPARATION OF LOWER ALKYL THIOSEMICARBAZIDES

The present invention relates to an improved process for the preparation of lower alkyl thiosemicarbazides.

Lower alkyl thiosemicarbazides are known intermediates for the synthesis of herbicides, as described, for example, in German DOS Nos. 1 670 925, 1 816 568, 1 901 672, 1 912 543, 2 028 778, 2 044 442 and 2 118 520 and United States Patent Application Ser. No. 729,933, filed Oct. 6, 1976, now U.S. Pat. No. 4,132,736. Thus, methyl thiosemicarbazide can be condensed with trimethylacetic acid and phosphorus oxychloride to form 2-methylamino-5-t-butyl-1,3,4-thiadiazole which can be reacted with methyl isocyanate to form the known herbicide 3-(5-t-butyl-1,3,4-thiadiazol-2-yl)-1,3-dimethylurea.

It is known that alkyl-triosemicarbazides are produced by reacting alkyl-isothiocyanates with hydrazine or hydrazine hydrate in the presence of a solvent (see G. Pulvermacher, Chemische Berichte 26, 2812 (1893) and 27, 622 (1894); K. A. Jensen, U. Anthoni B. Kaegi, Ch. Larsen, C. Th. Pedersen, Acta Chem. Scand. 22, 15 (1968).

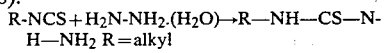
R-NCS+H$_2$N-NH$_2$.(H$_2$O)→R—NH—CS—NH—NH$_2$ R=alkyl

This process, however, has the disadvantage that alkyl isothiocyanates which are used as starting materials are expensive.

It is further known that alkyl thiosemicarbazides are obtained by reacting N-alkyl-dithio-carbamate esters with hydrazine in the presence of a solvent (see K. A. Jensen, U. Anthoni, B. Kaegi, Ch. Larsen, C. Th. Pedersen, Acta Chem. Scand 22, 16 (1968); Derwent CPI 66.231 S. Section E).

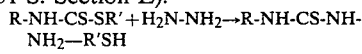
R-NH-CS-SR'+H$_2$N-NH$_2$→R-NH-CS-NH-NH$_2$—R'SH

R,R'=alkyl

This process also is not economical since in some cases the yields are only 65% and, in addition, the removal of the by-product alkyl mercaptans is very expensive.

In addition, it is also known that alkyl thiosemicarbazides are obtained by reacting N-unsubstituted dithiocarbazate esters with primary amines (see K. A. Jensen, H. Anthoni, B. Kaegi, Ch. Larsen, C. Th. Pedersen, Acta Chem. Scand. 22, 17 (1968); R. S. McElhinney, J. Chem. Soc. 1966, 950).

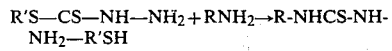
R'—CS—NH—NH$_2$+RNH$_2$→R-NHCS-NH-NH$_2$—R'SH

R,R'=alkyl

This process also is of little economical benefit since the yields are 40% and less and the separation of mercaptans requires special purification equipment.

It is further taught in German Pat. No. 832,891 that thiosemicarbazide and its alkyl, aryl, aralkyl and heterocyclic derivatives can be produced by reacting dithiocarbamates with hydrazine.

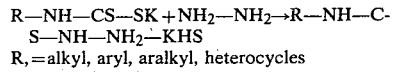
R—NH—CS—SK+NH$_2$—NH$_2$→R—NH—CS—NH—NH$_2$—KHS
R,=alkyl, aryl, aralkyl, heterocycles K=ammonia, potassium However, the alkyl compounds can only be obtained in an extremely low yield (under 1%) according to the process conditions described there. This has lead to the statement by K. A. Jensen, U. Anthoni, B. Kaegi, Ch. Larsen and C. Th. Pedersen in Acta Chem. Scand. 22, 17 (1968) that during heating of the hydrazinium salts of N-alkyl-dithiocarbamic acids in solvents the alkyl-thiosemicarbazides are not obtained.

In United States Application Ser. No. 729,933, now U.S. Pat. No. 4,132,736, supra, it is disclosed that alkyl thiosemicarbazides can be obtained by heating above 60° C. the hydrazinium salts of the corresponding N-alkyl-dithiocarbamic acid in a solvent in the presence of sulfur, i.e.

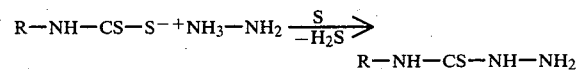
$$R-NH-CS-S^- \ {}^+NH_3-NH_2 \xrightarrow[-H_2S]{S} R-NH-CS-NH-NH_2$$

R=alkyl

While the yields are adequate, this requires use of a sulfur catalyst which complicates re-use of the end liquor, there is some undesirable by-product formation and the principal by-products are not in a re-usable form.

In Application Ser. No. 895,185, filed Apr. 10, 1978, now abandoned, there is described a process wherein an aqueous solution of an N-lower-alkyl-dithiocarbamic acid hydrazinium salt containing also ammonia and/or a lower alkyl amine is heated at a temperature up to about 60° C. to remove the ammonia and/or lower alkyl amine. Thereafter the residual solution is heated above 60° C. to effect decomposition to hydrogen sulfide and the lower alkyl thiosemicarbazide. While this is satisfactory, it involves two steps and is relatively time consuming.

It is accordingly an object of the present invention to provide a simplified process for the preparation of lower alkyl thiosemicarbazides which gives high yields, minimal amounts of undesired by-products which permits re-cycle of most of the by-products, and which can be carried out relatively rapidly.

These and other objects and advantages are realized in accordance with the present invention pursuant to which a solution of an N-lower alkyl-dithiocarbamic acid hydrazinium salt containing also ammonia and/or a lower alkyl amine is subjected to steam distillation thereby to effect pyrolysis and to remove ammonia and/or lower alkyl amine, water and hydrogen sulfide. Upon cooling of the distilland the desired lower alkyl thiosemicarbazide crystallizes out.

The hydrazinium salt solution is obtained by reaction of carbon disulfide with a lower alkyl amine, and optionally ammonia, in water followed by addition of hydrazine. The course of the reaction is believed to be as follows although the product of step (b) is not isolated and perhaps not even formed:

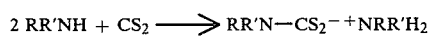
2 RR'NH + CS$_2$ ⟶ RR'N—CS$_2$$^-$ $^+$NRR'H$_2$   (a)

-continued

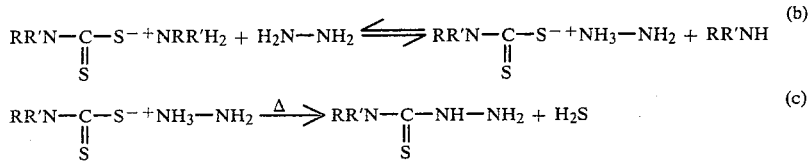

wherein
- R and R' each is hydrogen or lower alkyl provided that no more than about 20% of the R radicals are hydrogen when R' is hydrogen.
- R and R' are preferably hydrogen, methyl and/or ethyl.

The amine plus ammonia should be in excess relative to the carbon disulfide, and their reaction product may be provided in approximately stoichiometric amounts relative to the hydrazine although preferably it is provided in excess to ensure full utilization of the hydrazine which is the most expensive of the starting materials, e.g. up to about a 20% molar excess.

Reaction (a) is effected in aqueous media, preferably water per se, although inert organic liquids may be admixed therewith. The reaction can be effected at room temperature although somewhat higher or lower temperatures may be employed. The ammonia and/or amine by-product of reaction (b) and the hydrogen sulfide by-product of reaction (c) are simultaneously removed along with as much water as may be present and/or desired by steam distillation in accordance with the invention.

The temperature of distillation, which will also effect pyrolysis, should be at least about 85° C. and may go up to about 110° C. the temperature being directly related to the pressure, i.e. higher pressure requires a higher distillation temperature. While the absolute pressure may range from about 700 to 900 mm Hg or even higher or lower, advantageously it is substantially atmospheric to simplify operation. The temperature at such preferred pressure is from about 90° C. to 105° C.

The pyrolysis and stripping are comparatively rapid, little if any improvement being realized after 5 hours or even after 2 hours. Surprisingly the overall time for steps (b) and (c) is shorter than the time for each of the individual steps of Application Ser. No. 729,933, now U.S. Pat. No. 4,132,736.

After steam distillation, upon cooling the distilland to below about 65° C. crystallization commences even if additional water is added for fluidity or to ensure dissolution of any by-products which it is desired should not co-crystallize. Seed crystals of the product facilitate the crystallization. The product is recovered in high yield and purity.

Reaction (b) hereinabove behaves as if it is an equilibrium reaction favoring the original reactants. The range of steam distillation times possible (at least 1.25 to 5 hours) to obtain roughly equivalent results, supported by analysis of the overhead condensate (which display approximately equimolar evolution of $H_2S$ and amine after the excess amine is removed) indicates that the stripping of amine which favors formation of the hydrazinium salt is rate limiting in this procedure. Hydrazine (or hydrazinium) is found in low concentration (<1%) in the final mother liquor and it appears that during the strip/pyrolysis, the hydrazinium salt is present only in very small quantity.

The novel process improves over previously described processes in that:

(1) Less time is required for synthesis.
(2) Good conversion to product methylthiosemicarbazide (about 90% based on analysis of mother liquor and cake wash water) and reasonable recovered yield, about 77–82%, without further recovery of product from mother liquor.
(3) The filter cake wash water, recovered amine, and some mother liquor can be recycled.
(4) The mechanical and operational processing is simplified since vacuum, inert purging and catalysis are not required. Also, separate isolation of the hydrazinium alkyldithiocarbamate salt is not required since under the prevailing conditions apparently pyrolysis to product occurs simultaneously with the hydrazinium salt formation.

The invention will be further described in the following illustrative examples:

EXAMPLE 1

440 g of monomethylamine solution (5.68 moles) were charged to a 1 liter agitated reaction flask equipped with thermometer, reflux condenser and 250 ml addition funnel. The flask was cooled with a cooling bath containing water and dry ice while charging 202 g $CS_2$ (2.66 moles). The charge was made with agitation while maintaining the reactor temperature below 30° C., agitation continuing after the $CS_2$ charge until the $CS_2$ phase was consumed by reaction. 325 g of the total solution (642 g) were drained from the flask, leaving 317 g (1.31 moles methylammonium-4-methyldithiocarbamate).

394 g of water was charged to the 1 liter reactor and agitated and then 65 g hydrazine hydrate (1.30 moles) were added. The reflux condenser was modified to a take-off arrangement for distillation.

Using an agitated hot oil bath as the heating medium, the contents of the flask were heated to boiling and 571.5 g were removed by atmospheric distillation in approximately 1 hour. The distillation was completed in 1.25 hours. The batch was maintained at reflux (102°–104° C.) for 45 minutes following the distillation in order to monitor any off-gas evolution as evidence of latent pyrolysis and to determine $H_2S$ content of any off-gas. The off-gas collected gave a negative test to starch iodide paper, indicating no sulfur.

110 g of water were charged to the bottoms product which was then seeded with about 0.1 gram of crystals of methylthiosemicarbazide while cooling. Precipitation of crystals commenced at 65° C. Air cooling of the reactor was allowed until the slurry reached 40° C. after which it was water cooled to 20° C. and maintained 30 minutes. The product slurry was filtered in a Buechner filter funnel equipped with Whatman filter paper, the funnel being mounted on a filter flask to which aspirator vacuum was applied. 171.5 g of filtrate were recovered. The crude methylthiosemicarbazide wet cake was washed with 100 g of water yielding 122 g of wet cake.

After drying at 50° C. for approximately 16 hours in a cross-flow air oven, 108 g of cake were isolated of a purity of 95.2% and a melting point of 137.5° C. Net yield based on hydrazine was 75.3%.

EXAMPLE 2

788 g of water and 440 g of monomethylamine solution (5.68 moles) were charged to an agitated 2 liter flask equipped with thermometer and reflux condenser. With cooling and agitation 202 g of $CS_2$ (2.66 moles) were charged. Agitation was continued following the $CS_2$ addition until its phase in solution disappeared indicating reaction completion.

The reflux condenser arrangement was changed to a take-off for distillation. 130 g of hydrazine hydrate (2.60 moles) were charged to the reactor, and the resulting solution heated to boiling with a hot oil bath. 1036 g of distillate were collected in 2.6 hours. The oil bath was removed and 160 g water charged to the bottoms product solution. The batch was allowed to aircool overnight after seeding with methylthiosemicarbazide crystals. Following recovery of a crude cake by filtration, it was washed with 200 g of water, yielding 234 g of wet cake with 219.7 g of solids. The dry cake displayed a purity of 97.4% and a melting point of 135° C. Net yield based on hydrazine was 78.4%.

Equivalent results have been obtained using heating mantles over longer times in place of an oil bath.

EXAMPLE 3

8 gallons of water (66.6 lbs.) was charged to a 50 gallon jacketed reactor equipped with vapor condenser and thermocouple to monitor liquid temperature in the reactor. 91.2 lbs. of monomethylamine (1.177 lbs.-moles) was charged to the reactor followed by 2 gallons (16.7 lbs.) water to flush the charge line. 0.5 gallon of water (4.17 lbs) was charged to the reactor through the $CS_2$ charge line to check for possible obstructions. With cooling and agitation, 43 lbs. of $CS_2$ (0.566 lb-moles) was charged to the reactor in 98 minutes while maintaining the reactor contents at less than 31° C. 3 gallons of water (25 lbs.) were charged to the reactor in order to flush the $CS_2$ charge line and after 45 minutes agitation was stopped, consumption of the $CS_2$ then being complete.

28.3 lbs. of hydrazine hydrate (0.566 mole) was then charged with agitation, and the reactor contents heated by application of 30 psig steam to the jacket. 190 lbs. of distillate were collected in 4.9 hours. The reactor was cooled, seeded with methylthiosemicarbazide crystals and diluted with 4 gallons of water (33.3 lbs.). After cooling below 25° C. for 30 minutes the crude methylthiosemicarbazide cake was filtered into an open bowl Nutsche filter. The cake was washed with 5 gallons of water (41.7 lbs.) and 66.7 lbs. of wet cake were recovered. Upon drying a representative sample of wet cake, the equivalent dry cake weight was 48.5 lbs. The dry cake sample had a purity of 94.6%. Net yield based on hydrazine was 77.3%.

EXAMPLE 4

404 g of distillate from preparation of 4-methyl-3-thiosemicarbazide was charged to a 1 liter reaction flask with 105 g 50% sodium hydroxide solution; the distillate composition by weight was about 11% monomethylamine, 12% $H_2S$ with some by-product $NH_3$ in aqueous solution. The reaction flask was equipped with agitator, thermometer, heating-mantle, and take-off condenser arrangement for distillation. A 1 liter distillate receiver was charged with 113.5 g of 40% monomethylamine solution (1.46 moles) and 113.5 g water. Agitation and cooling were provided for the receiver as well as a dip tube from the take-off condenser which extended below the initial liquid level in the receiver.

The reaction flask was heated for atmospheric batch distillation of monomethylamine-water from the sodium sulfide-sodium hydrosulfide solution. Distillate was collected over a reaction flask temperature range of 82°–102° C. The final receiver contents were 437 g of approximately 21% monomethylamine solution (2.90 moles) with some by-product ammonia. The distilland contained the sodium sulfide solution.

The 437 g of distillate receiver contents were charged to a 1 liter agitated reaction flask equipped with thermometer, reflux condenser and cooling bath. Through an add funnel 101 g carbon disulfide (1.33 moles) were charged maintaining the reactor temperature at or below 30° C. and agitated until the $CS_2$ phase was consumed.

110 g recovered cake wash water from the previous 4-methyl-3-thiosemicarbazide synthesis was charged.

60 g hydrazine hydrate (1.20 moles) was charged and agitated. The reflux condenser was remounted to a take-off disposition for distillation, the condensed overheads being collected in a 1 liter receiver. The agitated reactor contents were heated by an electric heating mantle to the boiling point at atmospheric pressure (ca. 97° C.) and 424 g distillate collected (final reactor temperature 101° C.).

50 g water were charged while the batch cooled and seed crystals added at 70° C. After cooling to 20° C. and maintaining this temperature for 30 minutes, the precipitate was filtered, compressed, and washed with 100 ml water. After drying the cake as described in previous examples, 104 g of dry crude cake were recovered of 95.1% purity. Net yield on hydrazine hydrate basis was 78.5%.

The condensed overheads from this 4-methyl-3-thiosemicarbazide synthesis were treated according to the procedure outlined in the first two paragraphs of this example to obtain 420 g of amine solution (2.46 moles of amine; 0.25 moles ammonia) for recycle. Of this, 1.46 moles of monomethylamine came from charged stock solution, and 1.0 mole was freshly recovered monomethylamine; 0.25 mole of by-product ammonia were also present.

The above synthesis of 4-methyl-3-thiosemicarbazide was the fourth of four batches made in succession, each batch except the first using recovered amine solution from the previous batch.

The procedure as outlined in the examples hereinabove are unsuccessful if provision is not made to remove the amine or ammonia by distillation.

It will be appreciated that the instant specification and examples are set forth by way of illustration and not limitation, and that various modification and changes may be made without departing from the spirit and scope of the present invention.

What is claimed is:

1. A process for the production of a lower alkyl-thiosemicarbazide comprising distilling off water from an aqueous solution containing hydrazine and an N-lower alkyldithiocarbamic acid quaternary ammonium salt at about 85° to 110° C. and under a pressure of about 700 to 900 mm Hg for a time less than about 2 hours but sufficient to remove substantially the stoichiometric amount of hydrogen sulfide thereby to effect pyrolysis while distilling off water, lower alkyl amine and hydrogen sulfide, and cooling the distilland to form crystals of lower alkyl-thiosemicarbazide.

2. The process according to claim 1, wherein the quaternary ammonium salt solution is obtained by reaction of carbon disulfide with a lower alkyl amine in water, and the hydrazine is thereafter added.

3. The process according to claim 2, wherein ammonia is also reacted with the carbon disulfide along with the lower alkyl amine, the ammonia being present in up to about 20% of the total moles of ammonia plus lower alkyl amine.

4. The process according to claim 3, wherein the ammonia plus lower alkyl amine are present in the solution in at least about twice the molar amount of the hydrazinium salt.

5. The process according to claim 1, wherein the lower alkyl amine is methylamine.

6. The process according to claim 1, wherein methylamine and carbon disulfide are first reacted in water and hydrazine is thereafter added in up to about one-half the molar amount of the methylamine, steam distillation is effected at about 90° to 105° C., and the distilland is diluted with water and cooled to below about 65° C. to crystallize out the desired product.

* * * * *